United States Patent [19]

Abraham et al.

[11] Patent Number: 5,195,998
[45] Date of Patent: Mar. 23, 1993

[54] MEATAL GUARD

[75] Inventors: Bernard M. Abraham; Joel Z. Cornfield, both of Oak Park, Ill.

[73] Assignee: Adastra Corporation, Oak Park, Ill.

[21] Appl. No.: 748,246

[22] Filed: Aug. 21, 1991

[51] Int. Cl.⁵ ............................................. A61F 5/44
[52] U.S. Cl. .................................... 604/351; 604/349
[58] Field of Search ......................... 604/346–351, 604/170–174, 164, 106, 178

[56] References Cited

U.S. PATENT DOCUMENTS

| | | | |
|---|---|---|---|
| 3,898,993 | 8/1975 | Taniguchi | 604/172 |
| 3,908,635 | 9/1975 | Viek | 128/2 |
| 3,982,544 | 9/1976 | Dyck | 128/349 |
| 4,133,307 | 1/1979 | Ness | 128/75 |
| 4,237,894 | 12/1980 | Cohen | 128/349 |
| 4,269,310 | 5/1981 | Uson | 604/172 |
| 4,419,094 | 12/1983 | Patel | 604/174 |
| 4,419,097 | 12/1983 | Rowland | 604/174 |
| 4,432,758 | 2/1984 | Finegold | 604/104 |
| 4,775,362 | 10/1988 | Kronner | 604/96 |
| 4,784,647 | 11/1988 | Gross | 604/178 |
| 4,921,479 | 5/1990 | Grayzel | 604/53 |
| 4,990,138 | 2/1991 | Bacich et al. | 604/96 |
| 5,017,188 | 5/1991 | Marten et al. | 604/178 |

Primary Examiner—Randall L. Green
Assistant Examiner—R. Clarke
Attorney, Agent, or Firm—Michael, Best & Friedrich

[57] ABSTRACT

A penile meatal guard for a Foley-type catheter is composed of a material having a greater rigidity than the catheter and including a tubular section construction and arranged to slideably engage the catheter for insertion into the end of the urethra. An annular locating ring is disposed at the outer end of the tubular section for engaging the distal end of the penis.

11 Claims, 1 Drawing Sheet

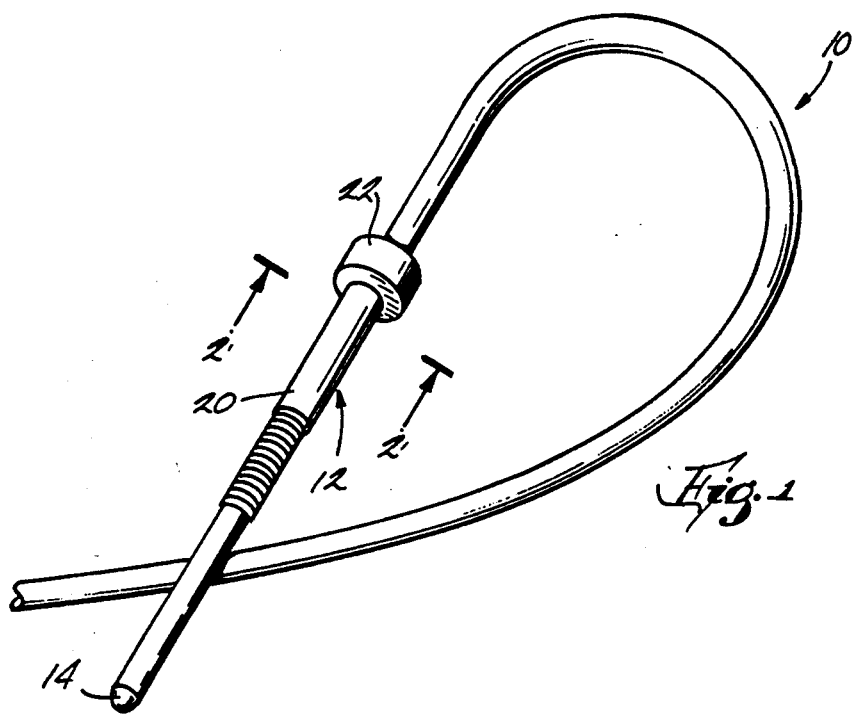
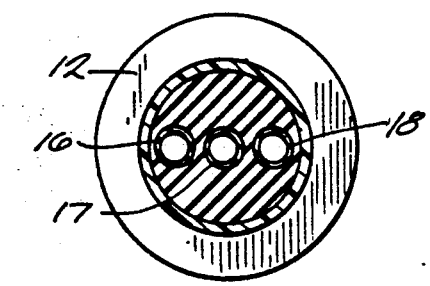
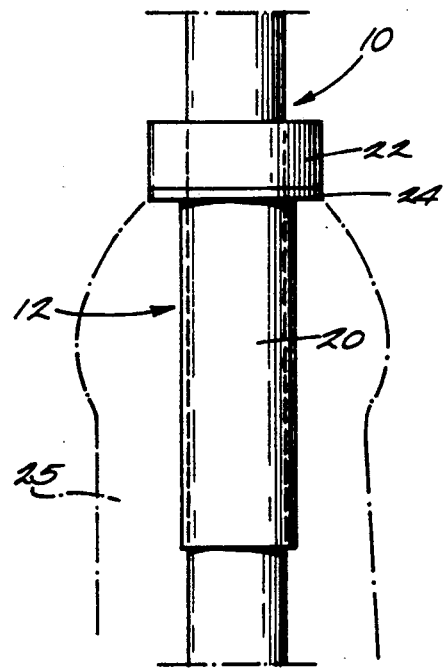

MEATAL GUARD

BACKGROUND OF THE INVENTION

This invention relates to catheters and more particularly to a meatal guard for Foley-type catheters.

It is sometimes necessary to catheterize male patients for bladder irrigation and drainage. For this purpose, indwelling, Foley-type catheters are commonly employed. Such catheters comprise a molded latex or silicone rubber tube, generally cylindrical in cross-section and which may include two or three separate flow paths. One of the paths is used to inflate a balloon at the base of the catheter tip in order to anchor the catheter in the bladder. A second passage is for drainage and a third, optional passage is for irrigation. The catheter is inserted through the urethra and may be required for anywhere from one day to several weeks. Although the catheter is very flexible, its bending modulus relative to the strength and sensitivity of the meatus is quite large. To avoid inadvertent stresses on the penile meatus, catheters are often taped to the patient's thigh. As a consequence of this practice, all stresses in the rubber generated by movement of the leg are supported by the tape and the tip of the penis. Pulling or stretching on this sensitive area is uncomfortable, at best, and is often painful. In addition, meatal stenosis or distal urethral stricture may result.

SUMMARY OF THE INVENTION

It is in object of the invention to provide a penile meatal guard for use with Foley-type catheters or the like.

A further object of the invention is to provide a meatal guard for Foley catheters which prevents stress in the penile meatus due to movement of the catheter.

Another object of the invention is to provide a meatal guard for Foley-type catheters or the like wherein modification of the catheter is not required.

These and other objects and advantages of the present invention will become more apparent from the detailed description thereof taken with the accompanying drawings.

BRIEF DESCRIPTION OF THE DRAWINGS

FIG. 1 is a perspective view showing a catheter and meatal guard according to the preferred embodiment of the invention;

FIG. 2 is a view taken along lines 2—2 of FIG. 1; and

FIG. 3 is a side view of the meatal guard illustrated in FIG. 1.

DETAILED DESCRIPTION OF THE PREFERRED EMBODIMENT

FIGS. 1 and 2 show a Foley-type catheter 10 and the meatal guard 12 according to the preferred embodiment of the invention. Foley-type catheters generally include an elongate tubular member which is circular in cross-section and formed of a rubber or rubber-like material, such as latex or silicone rubber. At one end, the catheter 10 includes a balloon 14 which, after the catheter has been positioned in the urethra, may be inflated for anchoring the catheter in the patient's bladder. At the other end, there is a coupling (not shown) for connecting the catheter to an appliance (not shown). As those skilled in the art will appreciate, the appliance is normally constructed and arranged for the selective delivery of sterile water for the inflation of balloon 14, for evacuating the bladder, and optionally for irrigating liquid.

As those skilled in the art will also appreciate, the catheter 10 includes at least two passages. In the illustrated embodiment shown in FIG. 2, catheter 10 includes three passages 16, 17 and 18, one of which is coupled to the balloon 14 and the other two for irrigation and drainage.

The meatal guard 12, according to the preferred embodiment of the invention, includes a hollow tubular section, 20 and an annular positioning ring 22 at one end. The guard 12 is formed of a plastic material which is relatively more rigid than the rubber-like material of which the catheter 10 is composed, An example of a plastic material found to be suitable is nylon, although it will be understood that any material having the required rigidity and other physical properties may be substituted. The internal diameter of the tubular section 20 will be sized to provide a sliding fit with the catheter 10, although the catheter 10 and guard 12 may be lubricated with a hydrophilic coating to facilitate relative sliding movement.

In use, the meatal guard is positioned slightly past the midpoint of the balloon 14 with the catheter providing a lead for insertion of the meatal guard into the patient's urethra. Once the guard is in position, the catheter is then pushed up the urethra to its proper position. At this point, there is sufficient friction between the catheter and the meatal guard to keep the guard in position. For added comfort, a soft pad 24 formed of a foam or other suitable material may be positioned between the positioning ring 22 and the tip of the patient's penis 25.

Meatal guard 20 has sufficient rigidity such that no stress is placed on the meatus even though the catheter may be flexed through relatively large angles.

While only a single embodiment of the invention has been illustrated and described, it is not intended to be limited thereby but only by the scope of the appended claims.

I claim:

1. A combination of a meatal guard and a urinary catheter constructed and arranged for insertion into the urethra of a male, said meatal guard comprising a hollow tubular section constructed and arranged to slideably engage the outer surface of the catheter for insertion into the end of a male patient's urethra and for being positioned between the catheter and the urethra, said catheter being formed of a material more flexible than said tubular section, and locating means projecting from the tubular section and positioned to be engaged by the tip of the patient's penis for limiting the insertion of the meatal guard into the urethra, said meatal guard acting to limit flexure of the catheter to reduce stress on the penile meatus.

2. The combination set forth in claim 1 wherein said locating means comprises an annular ring.

3. The combination set forth in claim 1 wherein a lubricant is disposed on the surfaces of the tubular member to facilitate sliding movement on the catheter and insertion into the urethra.

4. The combination set forth in claim 1 wherein the inner and outer surfaces of said tubular section are regular and unobstructed to facilitate sliding movement over said catheter and into said urethra.

5. A combination of a meatal guard and an elongate urinary catheter constructed and arranged for insertion into the urethra of a male patient, said catheter being composed of a flexible material, said meatal guard consisting of a tubular section telescopingly received on the outer surface of the catheter and slideable relative thereto for being positioned between said catheter and the urethra, said meatal guard also including locating means projecting laterally from said tubular member and adjacent one end thereof and positioned to be engaged by the tip of the patient's penis for limiting the insertion of the meatal guard into the urethra, said meatal guard being composed of a material having greater rigidity than that of the catheter whereby movement of said catheter relative to the urethra does not place undue stress on the end of the penile meatus.

6. The meatal guard set forth in claim 5 wherein said locating means comprises an annular ring.

7. The meatal guard set forth in claim 5 wherein a lubricant is disposed on the surfaces of the tubular member to facilitate sliding movement on the catheter and insertion into the urethra.

8. The combination set forth in claim 5 wherein the inner and outer surfaces of said tubular section are regular and unobstructed to facilitate sliding movement over said catheter and into said uretha.

9. A combination of a meatal guard and an elongate catheter of insertion into the urethra of a male patient and composed of a flexible material, said meatal guard consisting of a tubular section telescopingly received on the outer surface of the catheter and slideable relative thereto, said meatal guard also including a locating ring projecting laterally from said tubular member and adjacent one end thereof for limiting the insertion of the meatal guard into the urethra, said locating ring having a surface facing said tubular section and extending laterally therefrom, pad means disposed on said surface, said meatal guard being composed of a material maving greater rigidity than that of the catheter whereby movement of said catheter relative to the urethra does not place undue stress on the end of the penile meatus, and a lubricant disposed on the surfaces of the tubular member to facilitate sliding movement on the catheter and insertion into the urethra.

10. A combination of a meatal guard and an elongate urinary catheter constructed and arranged to be inserted into the urethra of a male patient, said guard comprising a hollow tubular section slidably received on the outer surface of the catheter for being positioned between the catheter and the end of a male patient's urethra, an annular ring projecting from the tubular section for limiting the insertion of the meatal guard into the urethra, said locating ring having a surface facing said tubular section and extending laterally therefrom, and pad means disposed on said surface.

11. A method of catheterizing a male patient and of protecting the end of a penile meatus, comprising the step of inserting a flexible catheter into the patient's urethra, positioning a tubular guard between the catheter and the urethra, said tubular guard having greater rigidity than the catheter, and locating the guard in the urethra by inserting the same into the urethra until the tip of the patient's penis engages a locator disposed on the outer surface of the tubular guard.

* * * * *

UNITED STATES PATENT AND TRADEMARK OFFICE
CERTIFICATE OF CORRECTION

PATENT NO. : 5,195,998
DATED : March 23, 1993
INVENTOR(S) : Abraham et al.

It is certified that error appears in the above–identified patent and that said Letters Patent is hereby corrected as shown below:

Column 3, line 25, the words "catheter of insertion" should read -- catheter for insertion--.

Signed and Sealed this

Thirty-first Day of May, 1994

Attest:

BRUCE LEHMAN

Attesting Officer

Commissioner of Patents and Trademarks